(12) United States Patent
Baril et al.

(10) Patent No.: US 11,529,170 B2
(45) Date of Patent: Dec. 20, 2022

(54) EXPANDABLE SURGICAL ACCESS PORT

(71) Applicant: Covidien LP, Mansfield, MA (US)

(72) Inventors: Jacob C. Baril, Norwalk, CT (US); Matthew A. Dinino, Newington, CT (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 260 days.

(21) Appl. No.: 16/861,460

(22) Filed: Apr. 29, 2020

(65) Prior Publication Data
US 2021/0338271 A1 Nov. 4, 2021

(51) Int. Cl.
*A61B 17/34* (2006.01)
(52) U.S. Cl.
CPC ................. *A61B 17/3423* (2013.01)
(58) Field of Classification Search
CPC ............ A61B 17/3417; A61B 17/3423; A61B 17/3431; A61B 17/3496; A61B 2017/3419; A61B 2017/3425; A61B 2017/3429; A61B 2017/3466
See application file for complete search history.

(56) References Cited

U.S. PATENT DOCUMENTS

| | | | |
|---|---|---|---|
| 2,468,985 A | 5/1949 | Krotz | |
| 2,648,985 A | 8/1953 | Mallory | |
| 3,674,007 A | 7/1972 | Freis | |
| 4,016,884 A | 4/1977 | Kwan-Gett | |
| 4,112,932 A | 9/1978 | Chiulli | |
| 4,183,357 A | 1/1980 | Bentley et al. | |
| 4,402,683 A | 9/1983 | Kopman | |
| 4,653,476 A | 3/1987 | Bonnet | |
| 4,863,430 A | 9/1989 | Klyce et al. | |
| 4,863,438 A | 9/1989 | Gauderer et al. | |
| 5,073,169 A | 12/1991 | Raiken | |
| 5,082,005 A | 1/1992 | Kaldany | |
| 5,125,897 A * | 6/1992 | Quinn | A61J 15/0065 604/99.03 |
| 5,159,921 A | 11/1992 | Hoover | |
| 5,176,697 A | 1/1993 | Hasson et al. | |

(Continued)

FOREIGN PATENT DOCUMENTS

| | | |
|---|---|---|
| CA | 2702419 A1 | 11/2010 |
| EP | 0807416 A2 | 11/1997 |

(Continued)

*Primary Examiner* — Anu Ramana
(74) *Attorney, Agent, or Firm* — Carter, DeLuca & Farrell LLP

(57) ABSTRACT

An expandable access port includes a port body transitionable between expanded and collapsed configurations. The expandable access port also includes a plug with a first portion secured to the port body and a second portion flexibly coupled to the first portion by an arm. The first portion has an orifice and the second portion has a post insertable into the orifice. A tube is attached to an inflation port on the first portion of the plug. The tube is attachable to a source of inflation fluid and in fluid communication with a chamber of the port body. A lumen extends through the port body and is configured to slidably receive the post or a surgical instrument therethrough. The lumen forms a fluid-tight boundary when the port body is in the expanded configuration.

18 Claims, 4 Drawing Sheets

(56) References Cited

U.S. PATENT DOCUMENTS

| | | |
|---|---|---|
| 5,183,471 A | 2/1993 | Wilk |
| 5,192,301 A | 3/1993 | Kamiya et al. |
| 5,242,409 A | 9/1993 | Buelna |
| 5,242,415 A | 9/1993 | Kantrowitz et al. |
| 5,257,973 A | 11/1993 | Villasuso |
| 5,257,975 A | 11/1993 | Foshee |
| 5,269,772 A | 12/1993 | Wilk |
| 5,295,658 A | 3/1994 | Atkinson et al. |
| 5,295,659 A | 3/1994 | Steele |
| 5,312,391 A | 5/1994 | Wilk |
| 5,312,417 A | 5/1994 | Wilk |
| 5,314,417 A | 5/1994 | Stephens et al. |
| 5,330,486 A | 7/1994 | Wilk |
| 5,334,143 A | 8/1994 | Carroll |
| 5,345,927 A | 9/1994 | Bonutti |
| 5,350,364 A | 9/1994 | Stephens et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,395,367 A | 3/1995 | Wilk |
| 5,437,683 A | 8/1995 | Neumann et al. |
| 5,443,453 A | 8/1995 | Walker et al. |
| 5,460,170 A | 10/1995 | Hammerslag |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A * | 9/1996 | Andersen ............ A61J 15/0042 604/174 |
| 5,556,387 A | 9/1996 | Mollenauer et al. |
| 5,577,993 A | 11/1996 | Zhu et al. |
| 5,584,850 A | 12/1996 | Hart et al. |
| 5,601,581 A | 2/1997 | Fogarty et al. |
| 5,634,911 A | 6/1997 | Hermann et al. |
| 5,634,937 A | 6/1997 | Mollenauer et al. |
| 5,649,550 A | 7/1997 | Crook |
| 5,651,771 A | 7/1997 | Tangherlini et al. |
| 5,653,705 A | 8/1997 | de la Torre et al. |
| 5,672,168 A | 9/1997 | de la Torre et al. |
| 5,683,378 A | 11/1997 | Christy |
| 5,685,857 A | 11/1997 | Negus et al. |
| 5,713,858 A | 2/1998 | Heruth et al. |
| 5,713,869 A | 2/1998 | Morejon |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | de la Torre et al. |
| 5,964,781 A | 10/1999 | Mollenauer et al. |
| 5,976,174 A | 11/1999 | Ruiz |
| 5,997,515 A | 12/1999 | de la Torre et al. |
| 6,017,355 A | 1/2000 | Hessel et al. |
| 6,018,094 A | 1/2000 | Fox |
| 6,024,736 A | 2/2000 | de la Torre et al. |
| 6,033,390 A * | 3/2000 | von Dyck ............... A61F 5/445 604/174 |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,534 B1 | 7/2001 | Butler et al. |
| 6,264,604 B1 | 7/2001 | Kieturakis et al. |
| 6,315,770 B1 | 11/2001 | de la Torre et al. |
| 6,319,246 B1 | 11/2001 | de la Torre et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,488,620 B1 | 12/2002 | Segermark et al. |
| 6,488,692 B1 | 12/2002 | Spence et al. |
| 6,527,787 B1 | 3/2003 | Fogarty et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,613,952 B2 | 9/2003 | Rambo |
| 6,623,426 B2 | 9/2003 | Bonadio et al. |
| 6,669,674 B1 | 12/2003 | Macoviak et al. |
| 6,676,639 B1 | 1/2004 | Ternstrom |
| 6,706,050 B1 | 3/2004 | Giannadakis |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B2 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,945,932 B1 | 9/2005 | Caldwell et al. |

(56) References Cited

U.S. PATENT DOCUMENTS

| | | | |
|---|---|---|---|
| 6,958,037 B2 | 10/2005 | Ewers et al. |
| 6,972,026 B1 | 12/2005 | Caldwell et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,153,261 B2 | 12/2006 | Wenchell |
| 7,163,510 B2 | 1/2007 | Kahle et al. |
| 7,192,436 B2 | 3/2007 | Sing et al. |
| 7,195,590 B2 | 3/2007 | Butler et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,084 B2 | 6/2007 | Skakoon et al. |
| 7,238,154 B2 | 7/2007 | Ewers et al. |
| 7,276,075 B1 | 10/2007 | Callas et al. |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,847 B2 | 5/2010 | Smith |
| 7,727,146 B2 | 6/2010 | Albrecht et al. |
| 7,736,306 B2 | 6/2010 | Brustad et al. |
| 7,758,500 B2 | 7/2010 | Boyd et al. |
| 7,766,824 B2 | 8/2010 | Jensen et al. |
| 7,787,963 B2 | 8/2010 | Geistert et al. |
| 7,798,898 B2 | 9/2010 | Luciano, Jr. et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,850,600 B1 | 12/2010 | Piskun |
| 7,896,889 B2 | 3/2011 | Mazzocchi et al. |
| 7,909,760 B2 | 3/2011 | Albrecht et al. |
| 7,951,117 B2 | 5/2011 | Wingardner, III et al. |
| 8,016,755 B2 | 9/2011 | Ewers et al. |
| 8,137,267 B2 | 3/2012 | Shelton, IV et al. |
| 8,157,786 B2 | 4/2012 | Miller et al. |
| 8,187,177 B2 | 5/2012 | Kahle et al. |
| 8,187,178 B2 | 5/2012 | Bonadio et al. |
| 8,226,553 B2 | 7/2012 | Shelton, IV et al. |
| 8,323,184 B2 | 12/2012 | Spiegal et al. |
| 8,425,410 B2 | 4/2013 | Murray et al. |
| 8,485,970 B2 | 7/2013 | Widenhouse et al. |
| 8,550,992 B2 | 10/2013 | Kleyman |
| 8,574,153 B2 | 11/2013 | Richard |
| 8,641,610 B2* | 2/2014 | Okoniewski ....... A61B 17/3423 600/207 |
| 8,663,271 B2* | 3/2014 | Mantell ....... A61M 39/0247 604/27 |
| 8,740,904 B2 | 6/2014 | Stopek |
| D712,034 S | 8/2014 | Richard et al. |
| 8,795,289 B2 | 8/2014 | Fowler et al. |
| 8,968,189 B2 | 3/2015 | Stellon et al. |
| 9,113,951 B2 | 8/2015 | Richard et al. |
| 9,226,771 B2* | 1/2016 | Tycast ............... A61M 25/0017 |
| 2001/0037053 A1 | 11/2001 | Bonadio et al. |
| 2002/0038077 A1 | 3/2002 | de la Torre et al. |
| 2002/0183594 A1 | 12/2002 | Beane et al. |
| 2003/0014076 A1 | 1/2003 | Mollenauer et al. |
| 2003/0073960 A1* | 4/2003 | Adams ............... A61B 17/3423 604/268 |
| 2003/0093104 A1 | 5/2003 | Bonner et al. |
| 2003/0105473 A1 | 6/2003 | Miller |
| 2003/0135091 A1 | 7/2003 | Nakazawa et al. |
| 2003/0149443 A1 | 8/2003 | Gaskill et al. |
| 2003/0236549 A1 | 12/2003 | Bonadio et al. |
| 2004/0015185 A1 | 1/2004 | Ewers et al. |
| 2004/0049099 A1 | 3/2004 | Ewers et al. |
| 2004/0049100 A1 | 3/2004 | Butler et al. |
| 2004/0073090 A1 | 4/2004 | Butler et al. |
| 2004/0092795 A1 | 5/2004 | Bonadio et al. |
| 2004/0092796 A1 | 5/2004 | Butler et al. |
| 2004/0111061 A1 | 6/2004 | Curran |
| 2004/0138529 A1 | 7/2004 | Wiltshire et al. |
| 2004/0167543 A1 | 8/2004 | Mazzocchi et al. |
| 2004/0267096 A1 | 12/2004 | Caldwell et al. |
| 2005/0020884 A1 | 1/2005 | Hart et al. |
| 2005/0043592 A1 | 2/2005 | Boyd et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0148823 A1 | 7/2005 | Vaugh et al. |
| 2005/0192483 A1 | 9/2005 | Bonadio et al. |
| 2005/0203346 A1 | 9/2005 | Bonadio et al. |
| 2005/0240082 A1 | 10/2005 | Bonadio et al. |
| 2005/0241647 A1 | 11/2005 | Nguyen et al. |
| 2005/0267419 A1 | 12/2005 | Smith |
| 2005/0288558 A1 | 12/2005 | Ewers et al. |
| 2006/0020241 A1 | 1/2006 | Piskun et al. |
| 2006/0030755 A1 | 2/2006 | Ewers et al. |
| 2006/0071432 A1 | 4/2006 | Staudner |
| 2006/0084842 A1 | 4/2006 | Hart et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0224164 A1 | 10/2006 | Hart et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0270911 A1 | 11/2006 | Voegele et al. |
| 2007/0088202 A1 | 4/2007 | Albrecht et al. |
| 2007/0088204 A1 | 4/2007 | Albrecht et al. |
| 2007/0088241 A1 | 4/2007 | Brustad et al. |
| 2007/0088258 A1 | 4/2007 | Wenchell et al. |
| 2007/0093695 A1 | 4/2007 | Bonadio et al. |
| 2007/0118175 A1 | 5/2007 | Butler et al. |
| 2007/0149859 A1 | 6/2007 | Albrecht et al. |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0225569 A1 | 9/2007 | Ewers et al. |
| 2007/0270654 A1 | 11/2007 | Pignato et al. |
| 2007/0270882 A1 | 11/2007 | Hjelle et al. |
| 2008/0027476 A1 | 1/2008 | Piskun |
| 2008/0033344 A1* | 2/2008 | Mantell ............. A61M 39/0247 604/27 |
| 2008/0048011 A1 | 2/2008 | Weller |
| 2008/0091143 A1 | 4/2008 | Taylor et al. |

(56) References Cited

U.S. PATENT DOCUMENTS

| | | |
|---|---|---|
| 2008/0097162 A1 | 4/2008 | Bonadio et al. |
| 2008/0097332 A1 | 4/2008 | Greenhalgh et al. |
| 2008/0161826 A1 | 7/2008 | Guiraudon |
| 2008/0200767 A1 | 8/2008 | Ewers et al. |
| 2008/0255519 A1 | 10/2008 | Piskun et al. |
| 2008/0319261 A1 | 12/2008 | Lucini et al. |
| 2009/0012477 A1 | 1/2009 | Norton et al. |
| 2009/0036745 A1 | 2/2009 | Bonadio et al. |
| 2009/0093752 A1 | 4/2009 | Richard et al. |
| 2009/0093850 A1 | 4/2009 | Richard |
| 2009/0131751 A1 | 5/2009 | Spivey et al. |
| 2009/0137879 A1 | 5/2009 | Ewers et al. |
| 2009/0182279 A1 | 7/2009 | Wenchell et al. |
| 2009/0187079 A1 | 7/2009 | Albrecht et al. |
| 2009/0221966 A1 | 9/2009 | Richard |
| 2009/0221968 A1 | 9/2009 | Morrison et al. |
| 2009/0227843 A1 | 9/2009 | Smith et al. |
| 2009/0270685 A1 | 10/2009 | Moreno et al. |
| 2009/0326330 A1 | 12/2009 | Bonadio et al. |
| 2009/0326332 A1 | 12/2009 | Carter |
| 2009/0326461 A1 | 12/2009 | Gresham |
| 2010/0063452 A1* | 3/2010 | Edelman ............ A61B 17/3421 604/174 |
| 2010/0100043 A1 | 4/2010 | Racenet |
| 2010/0113886 A1 | 5/2010 | Piskun et al. |
| 2010/0217087 A1 | 8/2010 | Bonadio et al. |
| 2010/0240960 A1 | 9/2010 | Richard |
| 2010/0249516 A1 | 9/2010 | Shelton, IV et al. |
| 2010/0249526 A1 | 9/2010 | Shelton, IV et al. |
| 2010/0280326 A1 | 11/2010 | Hess et al. |
| 2010/0298646 A1 | 11/2010 | Stellon et al. |
| 2010/0312061 A1 | 12/2010 | Hess et al. |
| 2010/0312063 A1 | 12/2010 | Hess et al. |
| 2011/0054260 A1 | 3/2011 | Albrecht et al. |
| 2011/0112371 A1 | 5/2011 | Smith et al. |
| 2014/0148648 A1* | 5/2014 | Tycast ............... A61M 25/1018 600/207 |

FOREIGN PATENT DOCUMENTS

| | | |
|---|---|---|
| EP | 0950376 A1 | 10/1999 |
| EP | 1312318 A1 | 5/2003 |
| EP | 1774918 A1 | 4/2007 |
| EP | 1932485 A1 | 6/2008 |
| EP | 2044889 A1 | 4/2009 |
| EP | 2044897 A1 | 4/2009 |
| EP | 2098182 A2 | 9/2009 |
| EP | 2181657 A2 | 5/2010 |
| EP | 2226025 A1 | 9/2010 |
| EP | 2229900 A1 | 9/2010 |
| EP | 2253283 A1 | 11/2010 |
| EP | 2289438 A1 | 3/2011 |
| WO | 9314801 A1 | 8/1993 |
| WO | 9404067 A1 | 3/1994 |
| WO | 9636283 A1 | 11/1996 |
| WO | 9733520 A1 | 9/1997 |
| WO | 9742889 A1 | 11/1997 |
| WO | 9916368 | 4/1999 |
| WO | 9922804 | 5/1999 |
| WO | 0032116 | 6/2000 |
| WO | 0032120 | 6/2000 |
| WO | 0108581 A2 | 2/2001 |
| WO | 0132116 A1 | 5/2001 |
| WO | 0149363 A1 | 7/2001 |
| WO | 0207611 A2 | 1/2002 |
| WO | 03034908 A2 | 5/2003 |
| WO | 03071926 | 9/2003 |
| WO | 2004043275 A1 | 5/2004 |
| WO | 2004054456 A1 | 7/2004 |
| WO | 2004075741 A2 | 9/2004 |
| WO | 2004075930 A2 | 9/2004 |
| WO | 2006019723 | 2/2006 |
| WO | 2006100658 A2 | 9/2006 |
| WO | 2006110733 A2 | 10/2006 |
| WO | 2006115893 A2 | 11/2006 |
| WO | 2008011358 A1 | 1/2008 |
| WO | 2008015566 A2 | 2/2008 |
| WO | 2008042005 | 4/2008 |
| WO | 2008093313 | 8/2008 |
| WO | 2008103151 A2 | 8/2008 |
| WO | 2008121294 A1 | 10/2008 |
| WO | 2009036343 A1 | 3/2009 |
| WO | 2010141409 A1 | 12/2010 |

* cited by examiner

EXPANDABLE SURGICAL ACCESS PORT

FIELD

The present disclosure relates to a surgical access port. More particularly, the present disclosure relates to an expandable surgical access port.

BACKGROUND

In minimally invasive surgical procedures, including endoscopic and laparoscopic surgeries, a surgical access device permits the introduction of a variety of surgical instruments into a body cavity. A surgical access device (e.g., a cannula or an access port) is introduced through an opening in tissue (e.g., a naturally occurring orifice or an incision) to provide access to an underlying surgical site in the body. Such procedures greatly reduce postoperative recovery time and minimize scarring to the patient. These procedures typically involve inserting one or more surgical access devices through the abdominal wall of the patient and insufflating the abdominal cavity. A laparoscope or other viewing instrument is inserted through one of the surgical access devices, or directly through the abdominal wall, to provide the clinician with an image of the abdominal cavity. The surgeon is then able to perform the procedure within the abdominal cavity by manipulating instruments that have been extended through the surgical access devices.

The number and type of instruments that a surgeon may use to complete a minimally invasive procedure is limited by the number, size and configuration of the surgical access devices that have been inserted through tissue. Because traditional surgical access devices are configured to provide access for only a single instrument, the simultaneous use of any additional instruments requires corresponding surgical access devices. For each additional surgical access device necessary to complete the procedure, an additional incision must be created. Each additional incision increases the length of the procedure and may prolong post-operative recovery time.

Therefore, it is desirable to provide a surgical access device for insertion through a single incision in the body of a patient which provides multiple ports for receipt of one or more surgical instruments.

SUMMARY

The present disclosure relates to an expandable access port having a port body transitionable between expanded and collapsed configurations. The port body includes inner and outer walls defining a chamber therebetween. A plug includes a first portion secured to the port body and a second portion flexibly coupled to the first portion via an arm. The first portion has a first orifice and the second portion has a first post insertable into the first orifice. A tube is attached to an inflation port on the first portion of the plug and attachable to a source of inflation fluid. The tube is in fluid communication with the chamber via the inflation port. A first lumen extends through the port body in correspondence with the first orifice. The first lumen is configured to slidably receive an elongate object therethrough. The expanded configuration of the port body forms a fluid-tight seal between the first lumen and the elongate object.

In aspects, the collapsed configuration of the port body may be configured to be inserted through an opening in tissue and the expanded configuration of the port body may be configured to form a fluid-tight seal with an opening in tissue.

In one aspect, the first portion of the plug may include a second orifice in alignment with a second lumen of the port body and the second portion of the plug may include a second post insertable into the second orifice of the first portion of the plug.

In an aspect, the collapsed configuration may include the first post disposed through the first orifice and into the first lumen.

In aspects, the expanded configuration of the port body may define a fluid-tight barrier in the second lumen.

In an aspect, the second portion of the plug may abut the first portion of the plug, the first post may be disposed in the first lumen, and the collapsed configuration of the port body may be insertable into an opening in tissue.

In an additional aspect, the second portion of the plug may be separable from the first portion of the plug in the expanded configuration of the port body.

In aspects, the elongate object may be the first post or a surgical instrument.

The present disclosure also relates to an expandable surgical access port. The surgical access port includes a port body having a chamber in fluid communication with a source of inflation fluid and a plug. The plug has a first portion attached to a proximal portion of the port body. The first portion has a first orifice and an inflation port. The plug also includes an arm and a second portion flexibly coupled to the first portion via the arm. The second portion also includes a first post that is insertable through the first orifice. A first lumen extends through the port body and the expanded configuration of the port body defines a fluid-tight boundary in the first lumen.

In aspects, the first orifice and the first lumen may be coaxial such that the first post is insertable into the first lumen.

In an aspect, a collapsed configuration of the port body may be configured to be inserted through an opening in tissue.

In a further aspect, the expandable surgical access port may include a surgical instrument disposed in the first lumen.

In one aspect, the expanded configuration of the port body may form a fluid-tight barrier between the surgical instrument and the first lumen.

In an aspect, the expanded configuration of the port body may be configured to form a fluid-tight boundary with the opening in tissue.

The present disclosure also relates to a method of accessing a surgical site. The method includes inserting a port body of an expandable access port through an opening in tissue where the port body includes inner and outer walls defining a chamber therebetween and a plug having a first portion with a first orifice extending therethrough, a second portion having a first post insertable into the first orifice, and an arm portion flexibly coupling the first and second portions. The method also includes introducing an inflation fluid into the chamber of the port body through an inflation port on the first portion of the plug thereby transitioning the port body to an expanded configuration, the expanded configuration of the port body forming a fluid-tight boundary with the opening, withdrawing the first post from the first orifice by separating the second portion of the plug from the first portion of the plug, and inserting a first surgical instrument through a first lumen defined through the port body, the first lumen forming a fluid-tight seal with the first surgical instrument.

In an aspect, the method may include inserting a second surgical instrument through a second lumen defined through the port body. The second lumen may form a fluid-tight seal with the second surgical instrument.

In aspects, the method may include removing the first surgical instrument from the first lumen.

In a further aspect, the method may include removing the inflation fluid from the chamber thereby transitioning the port body to a collapsed configuration.

Other features of the disclosure will be appreciated from the following description.

DESCRIPTION OF THE DRAWINGS

The accompanying drawings, which are incorporated in and constitute a part of this specification, illustrate aspects and features of the disclosure and, together with the detailed description below, serve to further explain the disclosure, in which.

DETAILED DESCRIPTION

Figure 1:
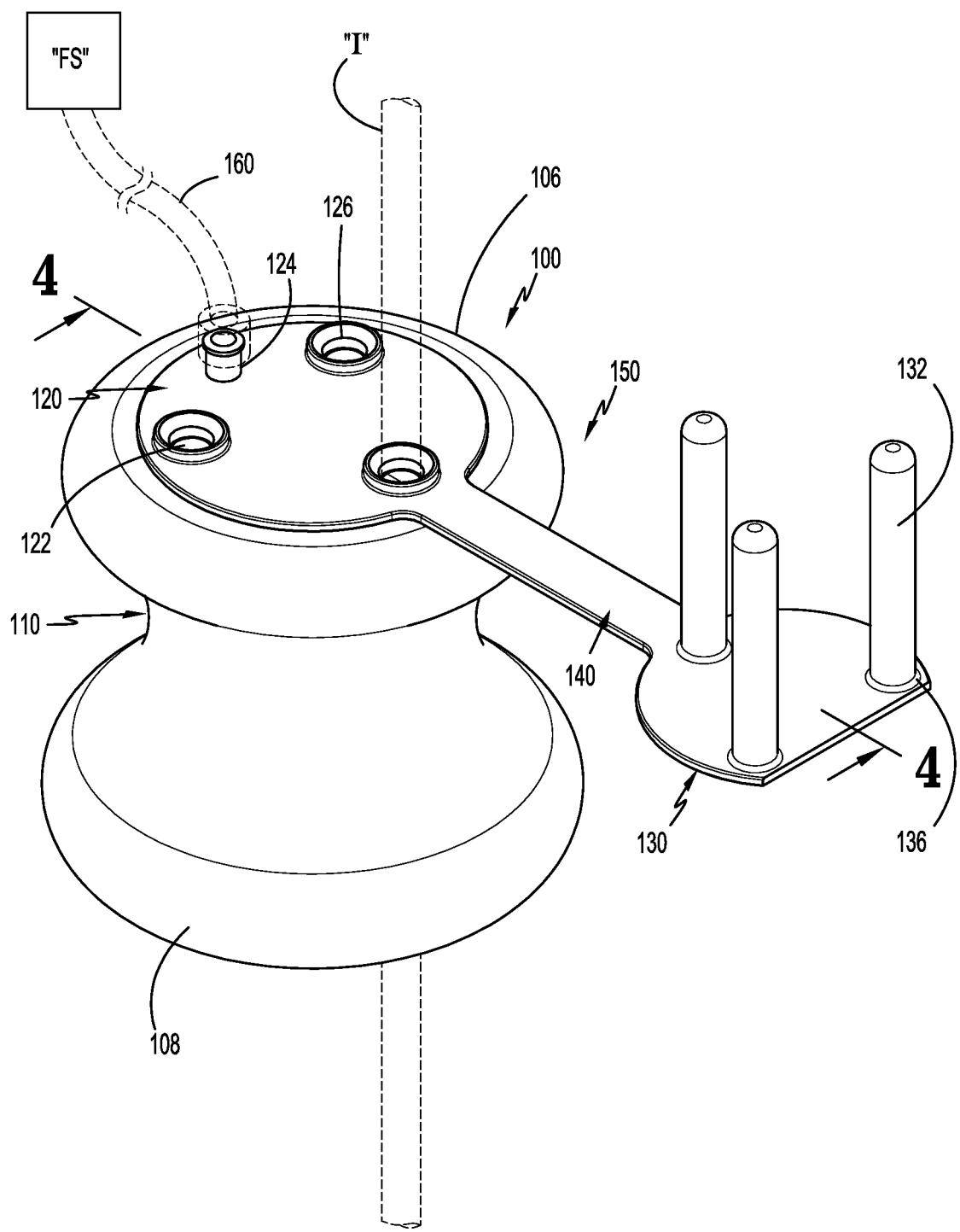
FIG. 1 is a top perspective view of an expandable access port in an expanded configuration with a portion of a plug removed from the expandable access port.

Aspects of the disclosure are described hereinbelow with reference to the accompanying drawings; however, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

Descriptions of technical features of an aspect of the disclosure should typically be considered as available and applicable to other similar features of another aspect of the disclosure. Accordingly, technical features described herein according to one aspect of the disclosure may be applicable to other aspects of the disclosure, and thus duplicative descriptions may be omitted herein. Like reference numerals may refer to like elements throughout the specification and drawings.

Figure 2:
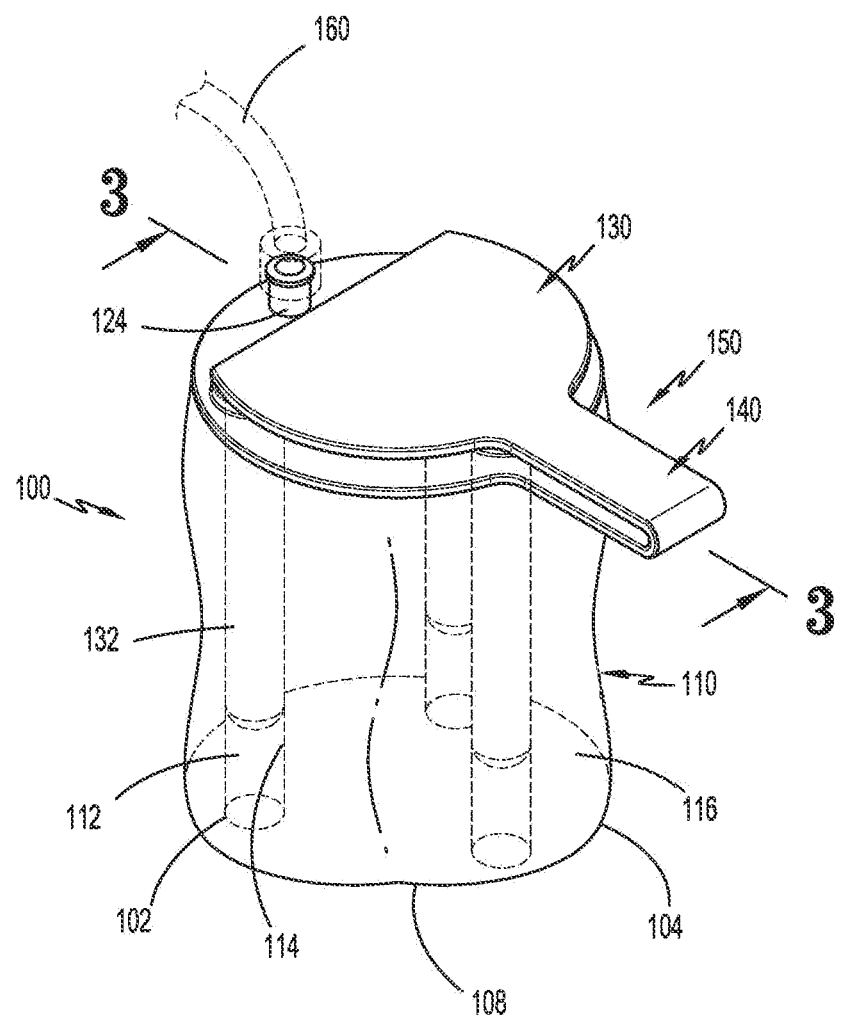
FIG. 2 is a top perspective view of the expandable access port of FIG. 1 in a collapsed configuration and the portion of the plug inserted into lumens of the expandable access port.
Figure 3:
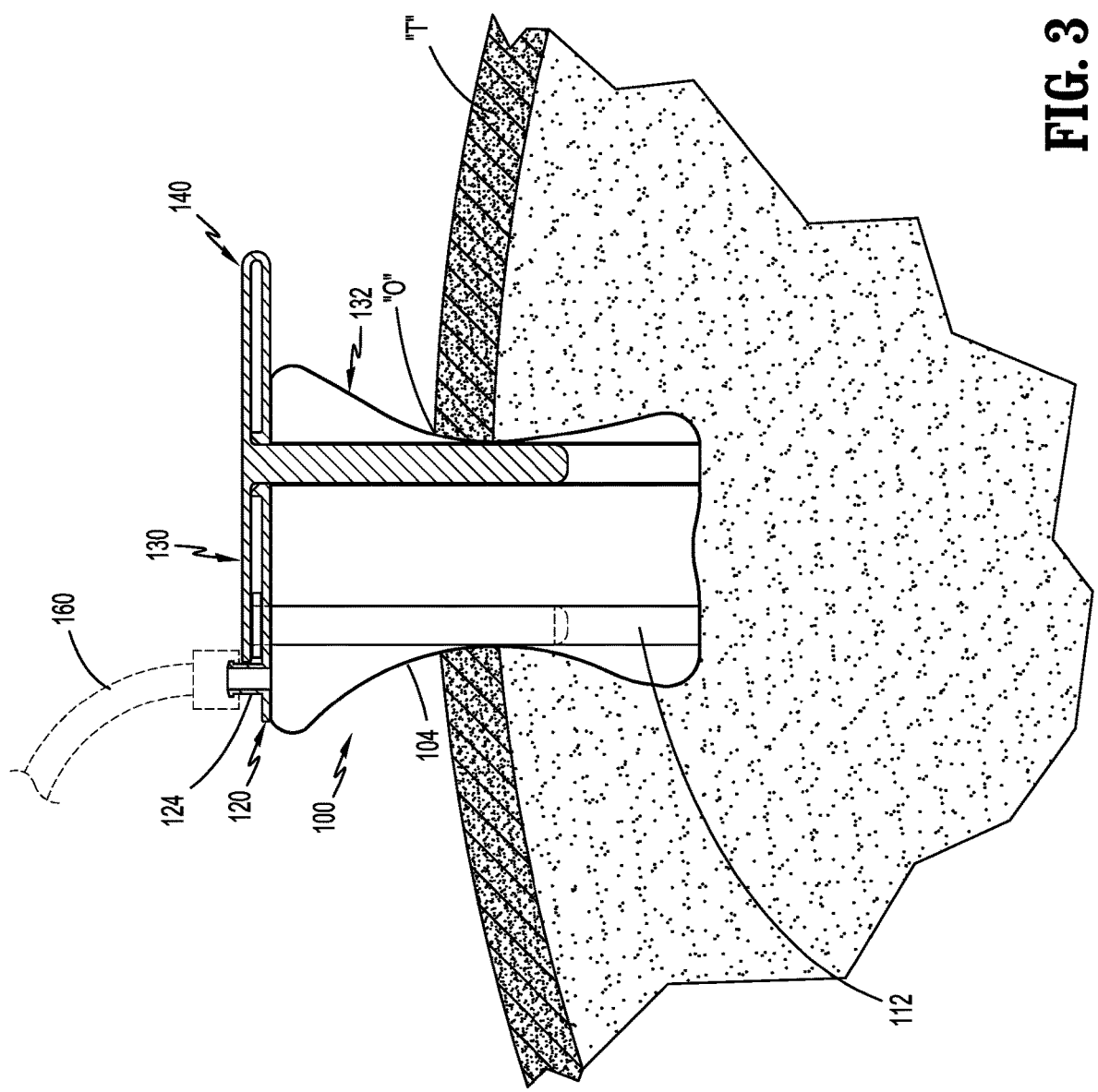
FIG. 3 is a side cross-sectional view of the expandable access port taken along section line 3-3 of FIG. 2 and inserted through an opening in tissue.

Initially, with reference to FIGS. 1 and 2, an expandable access port is shown generally as expandable access port 100. The expandable access port 100 includes a port body 110 that has inner and outer walls 102, 104 that define a chamber 116 therebetween. The port body 110 extends between proximal and distal ends 106, 108. The port body 110 is formed from a biologically compatible resilient elastomeric material that has a generally hourglass shape when in a fully expanded configuration (FIG. 1). One suitable example is silicone rubber. In a fully collapsed configuration (FIG. 2), the port body 110 is malleable such that the expandable access port 100 is insertable through an opening "O" (e.g., an incision or a naturally occurring opening) in tissue "T" (FIG. 3).

A plug 150 has a first portion 120 attached to the proximal end 106 of the port body 110 and a second portion 130 that is flexibly coupled to the first portion 120 with an arm 140. The first portion 120 of the plug 150 is generally planar and secured to the proximal end 106 of the port body 110. The first portion 120 may be secured to the proximal end 106 of the port body 110 using known techniques such as ultrasonic welding, adhesives, etc. As shown, the first portion 120 has three orifices 122 and an inflation port 124. Although shown with three orifices 122, it is contemplated that the first portion 120 could have a different number of orifices 122. By way of example only, the first portion 120 may only have a single orifice 122 or may have four or more orifices 122. Additionally, the inflation port 124 is in fluid communication with the chamber 116. One end of a tube 160 is attachable to the inflation port 124 and an opposing end of the tube 160 is attachable to a source "FS" of inflation fluid (e.g., liquid or gas) such as $CO_2$, air, or sterile saline. Introducing the inflation fluid through the tube 160 and the inflation port 124 into the chamber 116 transitions the port body 110 from the collapsed configuration to the expanded configuration. The second portion 130 of the plug is also generally planar and has posts 132 that correspond to the number of orifices 122 in the first portion 120. As shown, the second portion 130 has three posts 132 that correspond to the three orifices 122 of the first portion 120. In instances where the first portion 120 has fewer than three orifices 122, the second portion 130 has a corresponding number of posts 132. Likewise, if the first portion 120 has a greater number of orifices 122 (e.g., 5), the second portion 130 has a corresponding number of posts 132 (e.g., 5).

With specific reference to FIG. 2, the posts 132 of the second portion 130 of the plug 150 are insertable through the orifices 122 of the first portion 120 of the plug 150 such that the posts 132 are disposed in lumens 112 of the port body 110. Each lumen 112 is generally cylindrical and is defined by the intersection of the inner wall 102 and the outer wall 104. Each lumen 112 is coaxially aligned with one of the orifices 122 of the first portion 120 of the plug 150 (FIG. 3) and the number of lumens 112 corresponds to the number of orifices 122 in the first portion 120 of the plug 150. It follows that if there are a different number of orifices 122 in the first portion 120 of the plug that the number of lumens 112 will correspond to the number of orifices 122 in the first portion 120 of the plug 150. With the posts 132 of the second portion 130 of the plug 150 inserted into the orifices 122 of the first portion 120 of the plug 150 and the port body 110 in the collapsed configuration, the port body 110 is insertable through the opening "O" in tissue "T" (FIG. 3). Additionally, inserting the posts 132 through the orifices 122 in the first portion 120 of the plug 150 positions the posts 132 in the lumens 112 of the port body 110. The posts 132 being positioned in the corresponding lumens 112 provides sufficient rigidity to the port body 110 such that the port body 110 is insertable through the opening "O" in tissue "T".

In the absence of the posts 132 being inserted into the lumens 112 of the port body 110, fluids may travel through the lumens 112 between the orifices 122 of the first portion 120 of the plug 150 and the insertion end (i.e., distal end 108) of the port body 110. Inserting the posts 132 through the orifices 122 and into the lumens 112 may form a fluid-tight barrier where the posts 132 engage the orifices 122 as each post may have a shoulder 136 where each post 132 is attached to the second portion 130. The shoulders 136 fit into counter sunk recesses 126 in the orifices 122 thereby forming a fluid-tight seal when the posts 132 are inserted into the orifices 122. Thus, with the posts 132 inserted through the orifices 122 and into the lumens 112, the collapsed configuration of the port body 110 provides a fluid-tight boundary between its proximal and distal ends 106, 108. As such, once the port body 110 is inserted into the opening "O" in tissue, the expandable surgical access port 100 limits fluid flow through the opening "O" in both the collapsed configuration and the expanded configuration of the port body 110.

Referring now to FIG. 3, the port body 110 is shown in the collapsed configuration and partially inserted into tissue through the opening "O" in tissue "T". In the collapsed configuration, the outer wall 104 is reconfigurable such that the port body 110 may be manipulated such that the port body 110 is insertable through the opening "O" in tissue "T" and provide access to an underlying surgical site. By positioning the posts 132 of the second portion 130 of the plug 150 through the orifices 122 of the first portion 120 of the plug 150 and into the lumens 112 of the port body 110, the expandable surgical access port 100 has sufficient rigidity to allow insertion of the expandable surgical access port 100 into the opening "O" in tissue "T". Once the expandable surgical access port 100 is positioned in the opening "O" in tissue "T", inflation fluid may be introduced into the chamber 116 via the tube 160 attached to the inflation port 124 on the first portion 120 of the plug 150.

Figure 4:
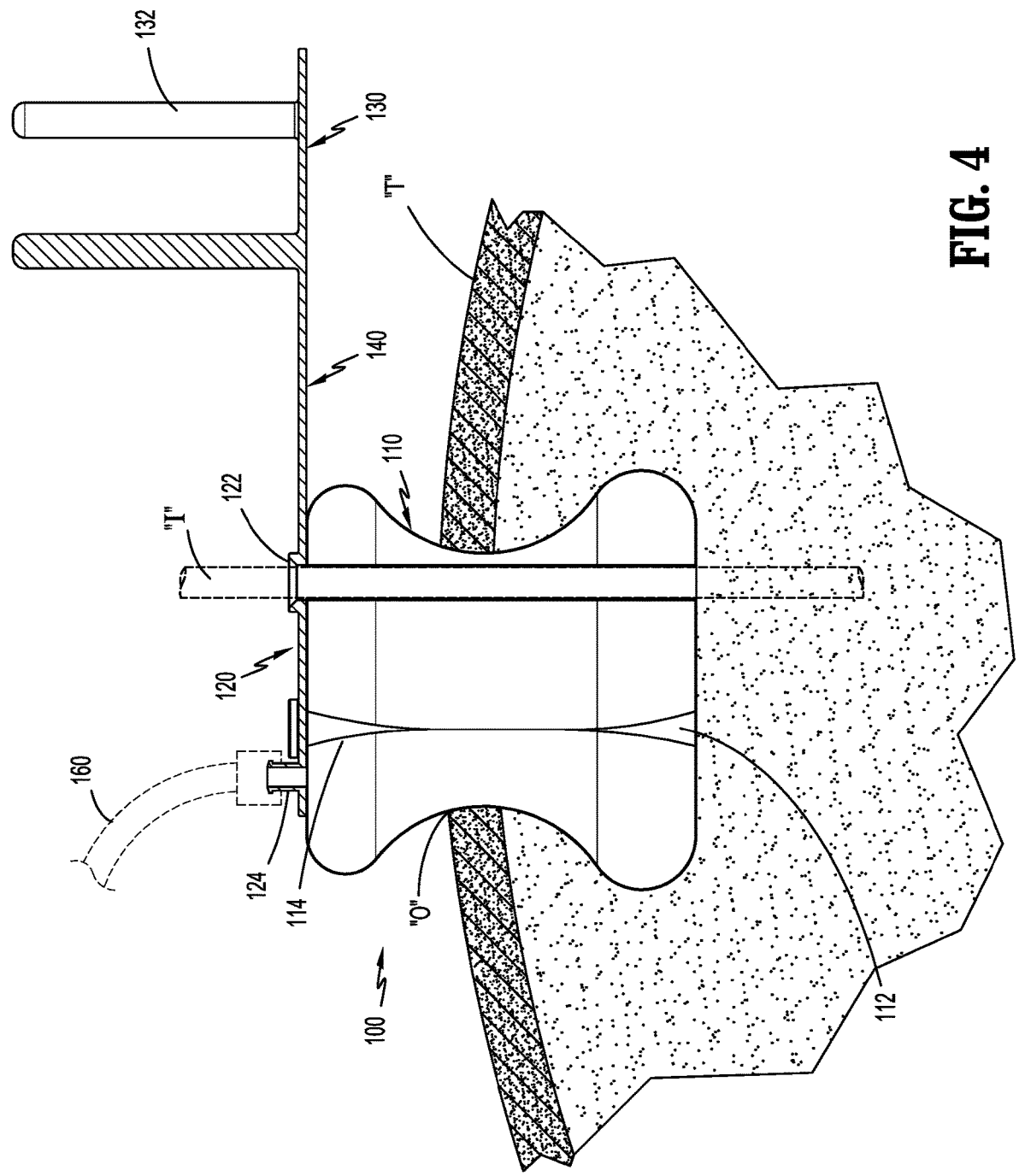
FIG. 4 is a side cross-sectional view of the expandable access port taken along section line 4-4 of FIG. 1 and inserted through an opening in tissue.

With reference now to FIG. 4, sufficient inflation fluid has been introduced into the chamber 116 of the port body 110 to transition the port body 110 from the collapsed configuration to the expanded configuration. Additionally, the second portion 130 of the plug 150 including the posts 132 has been separated from the first portion 120 of the plug 150. A first lumen 112 of the port body 110 lacks a post 132 or a surgical instrument "I" inserted therethrough and inner surfaces 114 of the first lumen 112 contact each other with sufficient force to define a fluid-tight boundary that inhibits fluid flow proximally and distally through the first lumen 112. As depicted in FIG. 4, an endoscopic surgical instrument (e.g., grasper, forceps, stapler, camera, etc.) "I" is inserted through a second lumen 112 of the port body 110. The inner surfaces 114 of the second lumen 112 engage the outer surface of the endoscopic surgical instrument "I" and define a fluid-tight boundary that inhibits fluid flow proximally and distally through the second lumen 112. Inserting another endoscopic surgical instrument "I" through the first lumen 112 causes the first lumen 112 to temporarily deform as the endoscopic surgical instrument "I" traverses through the first lumen 112 thereby maintaining a fluid-tight boundary in the first lumen 112. Once the endoscopic surgical instrument "I" is inserted through the first lumen 112, the first lumen 112 forms a fluid-tight boundary similar to that defined in the second lumen 112. Further, as the endoscopic surgical instrument "I" is removed from one of the lumens 112 of the port body 110, the inner surfaces 114 of the lumen 112 contact each other to define a fluid-tight boundary as the endoscopic surgical instrument "I" is removed thereby maintaining a fluid-tight boundary across the opening "O" in tissue "T". Additional lumens 112 in the port body 110 function in the same manner as the first and second lumens 112. Advantageously, the port body 110 maintains a fluid-tight boundary when inserted into the opening "O" in tissue "T" and transitioned to the expanded configuration.

Once the surgical procedure is completed, the clinician removes the expandable surgical access port 100 from the opening "O" in tissue "T". Removing the expandable surgical access port 100 from the opening "O" in tissue "T" is accomplished by evacuating the inflation fluid from the chamber 116 of the port body 110 by allowing the chamber 116 to vent to the surrounding environment or by actively withdrawing the inflation fluid from the chamber 116 via the inflation port 124. By removing the inflation fluid from the chamber 116, the port body 110 transitions from the expanded configuration (FIG. 4) to the collapsed configuration (FIG. 3). Since the posts 132 of the second portion 130 of the plug 150 are still separated from the lumens 112 of the port body 110 and the endoscopic surgical instrument(s) "I" are removed from the lumens 112 of the port body 110, the collapsed configuration of the port body 110 is easily removed from the opening "O" in tissue "T". Subsequently the opening "O" in tissue "T" is closed using known techniques.

Persons skilled in the art will understand that the devices and methods specifically described herein and illustrated in the accompanying drawings are non-limiting. It is envisioned that the elements and features may be combined with the elements and features of another without departing from the scope of the disclosure. As well, one skilled in the art will appreciate further features and advantages of the disclosure.

What is claimed is:

1. An expandable access port comprising:
   a port body transitionable between expanded and collapsed configurations, the port body including inner and outer walls defining a plurality of lumens extending through the port body;
   a plug including a first portion secured to the port body and a second portion flexibly coupled to the first portion via an arm, the first portion having a first orifice, and the second portion having a plurality of posts a first post of the plurality of posts insertable into the first orifice; and
   a tube attached to an inflation port on the first portion of the plug and attachable to a source of inflation fluid, the tube in fluid communication with the port body via the inflation port, wherein a first lumen of the plurality of lumens extends through the port body in correspondence with the first orifice, the first lumen of the plurality of lumens configured to slidably receive an elongate object through the first lumen of the plurality of lumens and the expanded configuration of the port body forms a fluid-tight seal between the first lumen of the plurality of lumens and the elongate object.

2. The expandable access port of claim 1, wherein the collapsed configuration of the port body is configured to be inserted through an opening in tissue and the expanded configuration of the port body is configured to form a fluid-tight seal with an opening in tissue.

3. The expandable access port of claim 2, wherein the collapsed configuration includes the first post disposed through the first orifice and into the first lumen of the plurality of lumens.

4. The expandable access port of claim 2, wherein the second portion of the plug abuts the first portion of the plug, the first post is disposed in the first lumen of the plurality of lumens, and collapsed configuration of the port body is insertable into an opening in tissue.

5. The expandable access port of claim 4, wherein the second portion of the plug is separable from the first portion of the plug in the expanded configuration of the port body.

6. The expandable access port of claim 1, wherein the first portion of the plug includes a second orifice in alignment with a second lumen of the plurality of lumens of the port body and the second portion of the plug includes a second post insertable into the second orifice of the first portion of the plug.

7. The expandable access port of claim 6, wherein the expanded configuration of the port body urges inner surfaces of the second lumen of the plurality of lumens into contact with each other and defines a fluid-tight barrier in the second lumen of the plurality of lumens.

8. The expandable access port of claim 1, wherein the elongate object is the first post or a surgical instrument.

9. An expandable surgical access port comprising:
    a port body in fluid communication with a source of inflation fluid, the port body including inner and outer walls defining a plurality of lumens extending through the port body;
    a plug having:
        a first portion attached to a proximal portion of the port body, the first portion having a first orifice and an inflation port,
        an arm, and
        a second portion flexibly coupled to the first portion via the arm and including a of plurality of posts a first post of the plurality of posts insertable through the first orifice; and
        the expanded configuration of the port body defining a fluid-tight boundary in a first lumen of the plurality of lumens and an elongate object placed into the first lumen.

10. The expandable surgical access port of claim 9, wherein the first orifice and the at least one lumen are coaxial such that the first post is insertable into the at least one lumen.

11. The expandable surgical access port of claim 9, wherein a collapsed configuration of the port body is configured to be inserted through an opening in tissue.

12. The expandable surgical access port of claim 11, wherein the expanded configuration of the port body is configured to form a fluid-tight boundary with the opening in tissue.

13. The expandable surgical access port of claim 9, further including a surgical instrument disposed in the at least one lumen.

14. The expandable surgical access port of claim 13, wherein the expanded configuration of the port body forms a fluid-tight barrier between the surgical instrument and the at least one lumen.

15. A method of accessing a surgical site comprising:
    inserting a port body of an expandable access port through an opening in tissue, the port body including:
        inner and outer walls defining a plurality of lumens, and
        a plug having a first portion with a first orifice extending through the plug, a second portion having a plurality of posts, a first post of the plurality of posts insertable into the first orifice, and an arm portion flexibly coupling the first and second portions;
    introducing an inflation fluid into the port body through an inflation port on the first portion of the plug thus transitioning the port body to an expanded configuration, the expanded configuration of the port body forming a fluid-tight boundary with the opening;
    withdrawing the first post from the first orifice by separating the second portion of the plug from the first portion of the plug; and
    inserting a first surgical instrument through a first lumen of the plurality of lumens defined through the port body, the first lumen of the plurality of lumens forming a fluid-tight seal with the first surgical instrument.

16. The method of claim 15, further including inserting a second surgical instrument through a second lumen of the plurality of lumens defined through the port body, wherein the second lumen forms a fluid-tight seal with the second surgical instrument.

17. The method of claim 15, further including removing the first surgical instrument from the first lumen of the plurality of lumens.

18. The method of claim 17, further including removing the inflation fluid from the port body thus transitioning the port body to a collapsed configuration.

\* \* \* \* \*